US011571123B2

(12) United States Patent
Ono

(10) Patent No.: US 11,571,123 B2
(45) Date of Patent: Feb. 7, 2023

(54) OPHTHALMOLOGIC APPARATUS AND METHOD OF CONTROLLING THE SAME

(71) Applicant: TOPCON CORPORATION, Tokyo (JP)

(72) Inventor: Yusuke Ono, Kita-ku (JP)

(73) Assignee: TOPCON CORPORATION, Tokyo (JP)

( * ) Notice: Subject to any disclaimer, the term of this patent is extended or adjusted under 35 U.S.C. 154(b) by 299 days.

(21) Appl. No.: 16/885,325

(22) Filed: May 28, 2020

(65) Prior Publication Data

US 2020/0288973 A1    Sep. 17, 2020

Related U.S. Application Data

(63) Continuation of application No. PCT/JP2018/042126, filed on Nov. 14, 2018.

(30) Foreign Application Priority Data

Dec. 28, 2017   (JP) .............................. JP2017-253571

(51) Int. Cl.
*A61B 3/00*   (2006.01)
*A61B 3/12*   (2006.01)
(Continued)

(52) U.S. Cl.
CPC .............. *A61B 3/12* (2013.01); *A61B 3/0008* (2013.01); *A61B 3/0025* (2013.01);
(Continued)

(58) Field of Classification Search
CPC .... A61B 3/12; A61B 3/10; A61B 3/14; A61B 3/0008; A61B 3/0025; A61B 3/0041;
(Continued)

(56) References Cited

U.S. PATENT DOCUMENTS

2006/0132711 A1   6/2006  Iwanaga
2007/0291277 A1  12/2007  Everett et al.
(Continued)

FOREIGN PATENT DOCUMENTS

EP    2 394 569 A1   12/2011
JP    02-237536 A     9/1990
(Continued)

OTHER PUBLICATIONS

Extended European Search Report dated Aug. 31, 2021 in European Patent Application No. 18895681.7, 8 pages.
(Continued)

*Primary Examiner* — Mustak Choudhury
(74) *Attorney, Agent, or Firm* — Xsensus LLP

(57) ABSTRACT

An ophthalmologic processing apparatus according to embodiments acquires data of a fundus of a subject's eye optically. The ophthalmologic apparatus includes a fixation system, an image acquisition unit, a specifying unit, and a determination unit. The fixation system is configured to project fixation light onto an eye of a subject. The image acquisition unit is configured to acquire an image of the fundus of the subject's eye in a state where the fixation light is projected by the fixation system. The specifying unit is configured to analyze the image acquired by the image acquisition unit to specify an image region corresponding to a predetermined site of the fundus. The determination unit is configured to determine whether or not the image region specified by the specifying unit is included within a predetermined range in the image acquired by the image acquisition unit.

14 Claims, 9 Drawing Sheets

(51) Int. Cl.
*A61B 3/10* (2006.01)
*A61B 3/15* (2006.01)

(52) U.S. Cl.
CPC ............ *A61B 3/0041* (2013.01); *A61B 3/102* (2013.01); *A61B 3/152* (2013.01)

(58) Field of Classification Search
CPC ....... A61B 3/0091; A61B 3/102; A61B 3/112; A61B 3/152; A61B 3/1025; A61B 3/1225; A61B 3/1241
See application file for complete search history.

(56) References Cited

U.S. PATENT DOCUMENTS

| | | | |
|---|---|---|---|
| 2010/0118132 A1 | 5/2010 | Yumikake et al. | |
| 2010/0149489 A1 | 6/2010 | Kikawa et al. | |
| 2011/0304821 A1* | 12/2011 | Tanassi | A61B 3/12 351/206 |
| 2015/0085252 A1 | 3/2015 | Fujimura et al. | |
| 2016/0143523 A1* | 5/2016 | Miyashita | A61B 3/0091 351/206 |
| 2016/0345822 A1 | 12/2016 | Fujimura et al. | |

FOREIGN PATENT DOCUMENTS

| | | | |
|---|---|---|---|
| JP | 10-234672 A | | 9/1998 |
| JP | 10234672 A | * | 9/1998 |
| JP | 2000-210257 A | | 8/2000 |
| JP | 2006-061328 A | | 3/2006 |
| JP | 2006-174889 A | | 7/2006 |
| JP | 2008-289579 A | | 12/2008 |
| JP | 2008-289642 A | | 12/2008 |
| JP | 2013-248376 A | | 12/2013 |
| JP | 2014-039870 A | | 3/2014 |
| JP | 2016-158721 A | | 9/2016 |

OTHER PUBLICATIONS

International Search Report and Written Opinion dated Feb. 12, 2019 for PCT/JP2018/042126 filed on Nov. 14, 2018, 9 pages including English Translation of the International Search Report.
Office Action dated Jan. 18, 2022, in corresponding Japanese patent Application No. 2017-253571, 9 pages.
Japanese Office Action dated Sep. 6, 2022, in corresponding Japanese Patent Application No. 2017-253571, 4 pp.

* cited by examiner

OPHTHALMOLOGIC APPARATUS AND METHOD OF CONTROLLING THE SAME

CROSS-REFERENCE TO RELATED APPLICATIONS

The present application is a continuation application of International Patent Application No. PCT/JP2018/042126, filed Nov. 14, 2018, which claims priority to Japanese Patent Application No. 2017-253571, filed Dec. 28, 2017. The contents of these applications are incorporated herein by reference in their entirety.

FIELD

The disclosure relates to an ophthalmologic apparatus and a method of controlling the same.

BACKGROUND

Types of ophthalmologic apparatuses include ophthalmologic imaging apparatuses for obtaining images of a subject's eye, ophthalmologic measuring apparatuses for measuring characteristics of a subject's eye, and ophthalmologic therapy apparatuses for treating a subject's eye.

Examples of the ophthalmologic imaging apparatuses include an optical coherence tomography (OCT) apparatus for capturing tomographic images using OCT, a fundus camera for photographing the fundus, a scanning laser ophthalmoscope (SLO) for capturing images of the fundus by laser scanning with the use of a confocal optical system, slit lamp microscopes, operating microscopes, and the like.

Examples of the ophthalmologic measuring apparatuses include eye refraction examination apparatuses (refractometer, keratometer) for measuring the refractive properties of the subject's eye, tonometers, specular microscopes for obtaining the properties of the cornea (corneal thickness, cell distribution, etc.), wave-front analyzers for obtaining the aberration information of the subject's eye using a Hartmann-Shack sensor, perimeters for measuring states of visual field, mircoperimeters, and the like.

Examples of the ophthalmologic therapy apparatuses include laser therapy apparatuses for projecting laser light onto the site to be treated such as diseased are, surgical apparatuses for specific purpose (cataract surgery, keratorefractive surgery etc.), surgical microscopes, and the like.

Many ophthalmologic apparatuses are provided with a configuration for presenting a fixation target to a subject's eye (or its fellow eye). The fixation target has a function of guiding the line of sight to acquire data of a desired site of the subject's eye, a function of fixing the subject's eye during data acquisition, and the like.

Further, ophthalmologic apparatuses having a function called an auto shoot, which detects that alignment or the like is in a suitable state and automatically starts acquisition of data of the subject's eye. In the auto shoot, the acquisition of data of the subject's eye is triggered by detecting that the indicator indicating a state of the alignment (bright spot image, characteristic site, etc.) enters within a predetermined range. In such an ophthalmologic apparatus, data of a desired site of the subject's eye can be automatically acquired by controlling a presentation position of the fixation target.

SUMMARY

One aspect of some embodiments is an ophthalmologic apparatus acquiring data of a fundus of a subject's eye optically. The ophthalmologic apparatus includes a fixation system configured to project fixation light onto an eye of a subject an image acquisition unit configured to acquire an image of the fundus of the subject's eye in a state where the fixation light is projected by the fixation system a specifying unit configured to analyze the image acquired by the image acquisition unit to specify an image region corresponding to a predetermined site of the fundus; and a determination unit configured to determine whether or not the image region specified by the specifying unit is included within a predetermined range in the image acquired by the image acquisition unit.

Another aspect of some embodiments is a method of controlling an ophthalmologic apparatus acquiring data of a fundus of a subject's eye optically. This method of controlling the ophthalmologic apparatus includes projecting fixation light onto an eye of a subject using a fixation system acquiring an image of the fundus of the subject's eye in a state where the fixation light is projected by the fixation system analyzing the acquired image to specify an image region corresponding to a predetermined site of the fundus; and determining whether or not the specified image region is included within a predetermined range in the acquired image.

DETAILED DESCRIPTION

Figure 1:
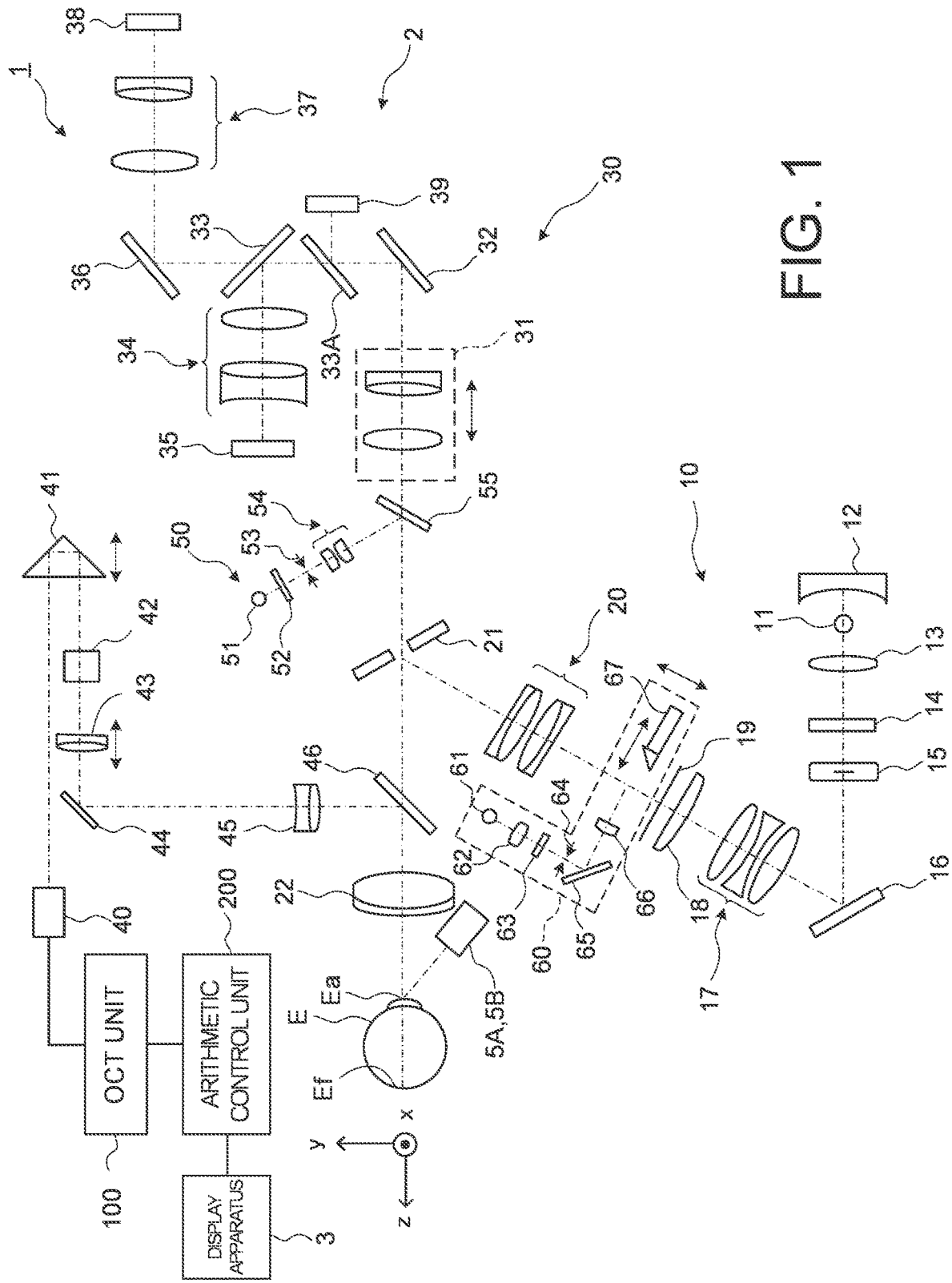
FIG. 1 is a schematic diagram illustrating an example of a configuration of an ophthalmologic apparatus according to embodiments.

The data of the desired site can not be acquired in case that the subject is not gazing at the fixation target even if the fixation target is presented. For example, when there is a problem in the visual acuity of the subject's eye or when the subject is an aged person or a child, the functions described above of the fixation target may not be sufficiently fulfilled. In addition, voluntary or involuntary movement of the subject's eye may interfere with fixation. Such a phenomenon is called fixation loss or the like.

According to some embodiments of the present invention, an ophthalmologic apparatus and a method of controlling the ophthalmologic apparatus capable of appropriately dealing with fixation loss can be provided.

Referring now to the drawings, exemplary embodiments of an ophthalmologic apparatus and a method of controlling the ophthalmologic apparatus according to some embodiments of the present invention are described below. Any of the contents of the documents cited in the present specification and arbitrary known techniques may be applied to the embodiments below.

The ophthalmologic apparatus according to some embodiments includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes any one or more of a fundus camera, a scanning laser ophthalmoscope, a slit lamp microscope, a surgical microscope, and the like, for example. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

In the following embodiments, the ophthalmologic apparatus according to the embodiments includes an optical coherence tomography (OCT) and a fundus camera. Although swept source OCT is employed as OCT, the type of OCT is not limited to the swept source OCT. It is also possible to employ other types of OCT (spectral domain OCT, time domain OCT, en-face OCT, or the like).

<Configuration>
[Optical System]

As shown in FIG. 1, the ophthalmologic apparatus 1 includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. Furthermore, the ophthalmologic apparatus 1 includes a pair of anterior segment cameras 5A and 5B.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

[Fundus Camera Unit 2]

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a photographic image, or the like. The observation image is obtained by moving image shooting using near infrared light. The photographic image is a still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after penetrating a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, penetrates a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, penetrates the dichroic mirror 46, passes through the hole part formed in the center area of the perforated mirror 21, penetrates a dichroic mirror 55. The returning light penetrating the dichroic mirror 55 travels through a photography focusing lens 31 and is reflected by a mirror 32. Further, this returning light penetrates a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) output from the imaging light source 15 is projected onto the fundus Ef via the same route as that of the observation illumination light. Returning light of the imaging illumination light from the subject's eye E is guided to the dichroic mirror 33 via the same route as that of the observation illumination light, penetrates the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmologic apparatus 1 according to some embodiments includes GUI (Graphical User Interface) and the like for designating at least one of such fixation positions. The ophthalmologic apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmologic apparatus 1 may be provided with one or more external fixation light sources. One of the one or more external fixation light sources can project fixation light onto a fellow eye of the subject's eye E. A projection position of the fixation light on the fellow eye can be changed. By changing the projection position of the fixation light on the fellow eye, the fixation position of the subject's eye E can be changed. The projection position by the external fixation light source(s) may be the same as the projection position of the subject's eye E using the LCD 39. For example, the movable fixation target can be generated by selectively turning on a plurality of external fixation light sources. Alternatively, the movable fixation target can be generated using one or more movable external fixation light sources.

The alignment optical system 50 generates an alignment indicator for alignment of the optical system with respect to the subject's eye E. Alignment light output from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 penetrates the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To conduct focus adjustment, the reflective surface of the reflection rod 67 is arranged in a slanted position on the illumination optical path. Focus light output from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, penetrates the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof The dichroic mirror 46 combines an optical path for fundus photography and an optical path for OCT. The dichroic mirror 46 reflects light of wavelength band used in OCT, and transmits light for fundus photography. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate with the pupil of the subject's eye E. The optical scanner 42 deflects the measurement light LS traveling along the OCT optical path. The optical scanner 42 is a galvano scanner capable of scanning two-dimensionally, for example.

The OCT focusing lens 43 is moved along the optical path of the measurement light LS in order to perform focus adjustment of the optical system for OCT. The movement of the photography focusing lens 31, the movement of the focus optical system 60, and the movement of the OCT focusing lens 43 can be controlled in conjunction with each other.

[Anterior Segment Cameras 5A and 5B]

The anterior segment cameras 5A and 5B are used for obtaining relative position between the optical system of the ophthalmologic apparatus 1 and the subject's eye E in the same manner as the invention disclosed in Japanese Unexamined Patent Application Publication No. 2013-248376. The anterior segment cameras 5A and 50B are located on a surface of a housing (fundus camera unit 2 etc.) in which the optical system is stored to face the subject's eye E. The ophthalmologic apparatus 1 obtains the three-dimensional relative position between the optical system and the subject's eye E, by analyzing two anterior segment images acquired substantially simultaneously from different directions by the anterior segment cameras 5A and 5B. The analysis of the two anterior segment images may be the same as the analysis disclosed in Japanese Unexamined Patent Application Publication No. 2013-248376. Furthermore, it should be noted that the number of the anterior segment cameras may be arbitrary (equal to or more than two).

In the present examples, the position of the subject's eye E (that is, the relative position between the subject's eye E and the optical system) is obtained using two or more anterior segment cameras. However, a method of obtaining the position of the subject's eye E is not limited to this. For example, the position of the subject's eye E can be obtained by analyzing the front image (for example, the observation image of the anterior segment Ea) of the subject's eye E. Alternatively, means for projecting an indicator onto the cornea of the subject's eye E can be provided. Thereby, the position of the subject's eye E can be obtained based on the projection position of the indicator (that is, the detection state of the corneal reflection light flux of this indicator).

[OCT Unit 100]

Figure 2:
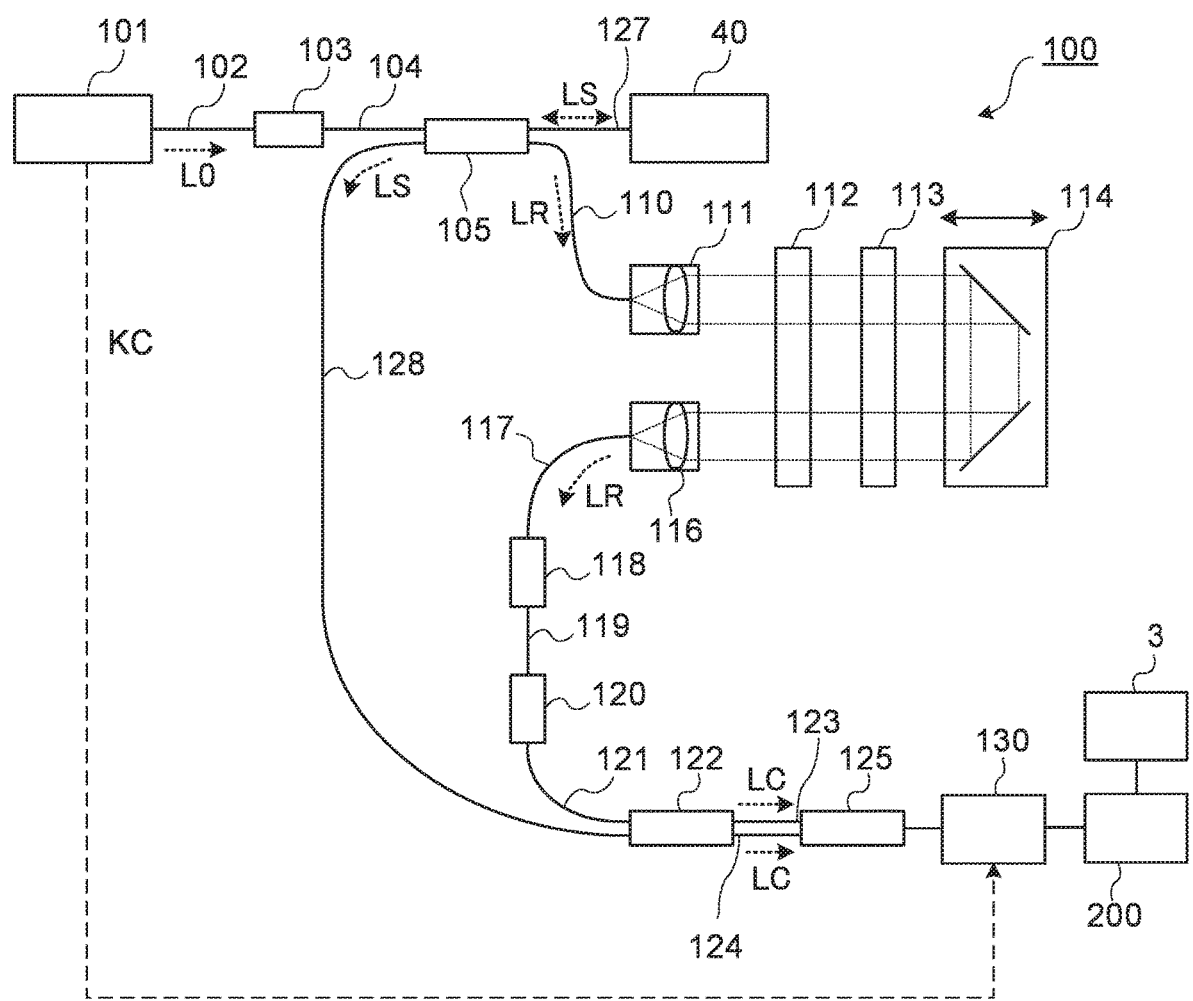
FIG. 2 is a schematic diagram illustrating an example of a configuration of the ophthalmologic apparatus according to the embodiments.

As illustrated by an example in FIG. 2, the OCT unit 100 is provided with an optical system for performing swept source OCT. This optical system includes an interference optical system. This interference optical system has a function that splits light from the wavelength tunable type (wavelength sweeping type) light source into measurement light and reference light, a function that makes the returning light of the measurement light from the subject's eye E and the reference light having traveled through a reference optical path interfere with each other and generates interference light, and a function that detects the interference light. The detection result (detection signal) of the interference light obtained by the interference optical system is a signal indicating a spectrum of the interference light, and is sent to the arithmetic control unit 200.

The light source unit 101 includes a near-infrared tunable laser which changes the wavelength of the emitted light at high speed, for example. Light L0 output from the light source unit 101 is guided to the polarization controller 103 by the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into the parallel light beam travels through the optical path length changing unit 41, the optical scanner 42, the OCT focusing lens 43, the mirror 44, and the relay lens 45. The measurement light LS having traveled through the relay lens 45 is reflected by the dichroic mirror 46, is refracted by the objective lens 22, and is irradiated onto the subject's eye E. The measurement light LS is scattered and reflected at various depth positions of the subject's eye E. Returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is a balanced photodiode, for example. The balanced photodiode includes a pair of photodetectors in which each photodiode detects each of the pair of interference light LC. The balanced photodiode outputs the difference between a pair of detection results acquired by the pair of photodetectors. The detector 125 sends the output (detection signal) to a DAQ (data acquisition system) 130.

A clock KC is supplied from the light source unit 101 to the DAQ 130. The clock KC is generated in the light source unit 101 in synchronization with the output timing of each wavelength within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic control unit 200.

In the present examples, both the optical path length changing unit 41 that changes the length of the optical path of the measurement light LS (i.e., measurement optical path or measurement arm) and the corner cube 114 that changes the length of the optical path of the reference light LR (i.e., reference optical path or reference arm) are provided. Alternatively, any one of the optical path length changing unit 41 and the corner cube 114 may be provided. The difference between the measurement optical path length and the reference optical path length can be changed using other optical members.

[Control System]

Figure 3:
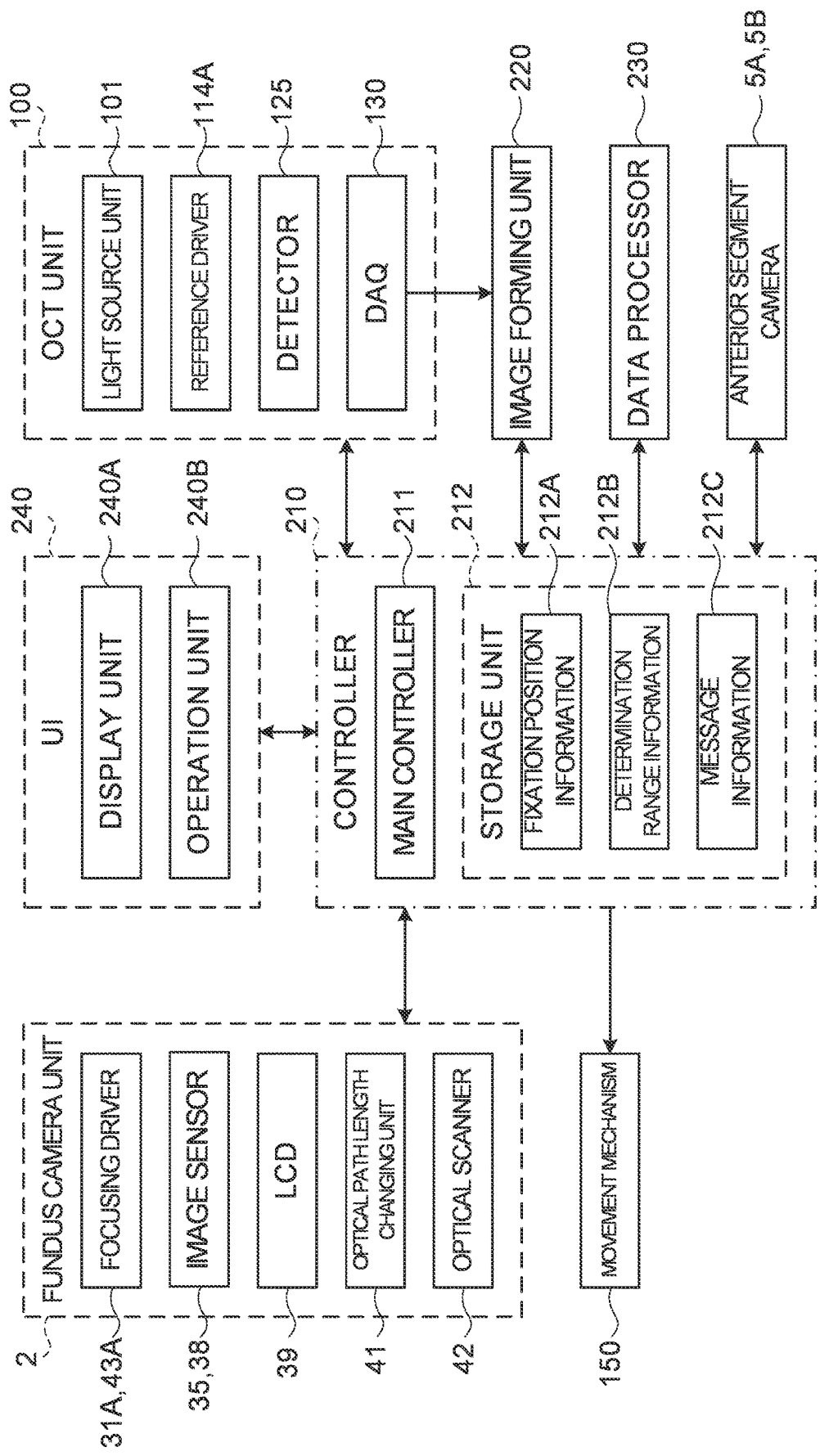
FIG. 3 is a schematic diagram illustrating an example of a configuration of the ophthalmologic apparatus according to the embodiments.
Figure 4:
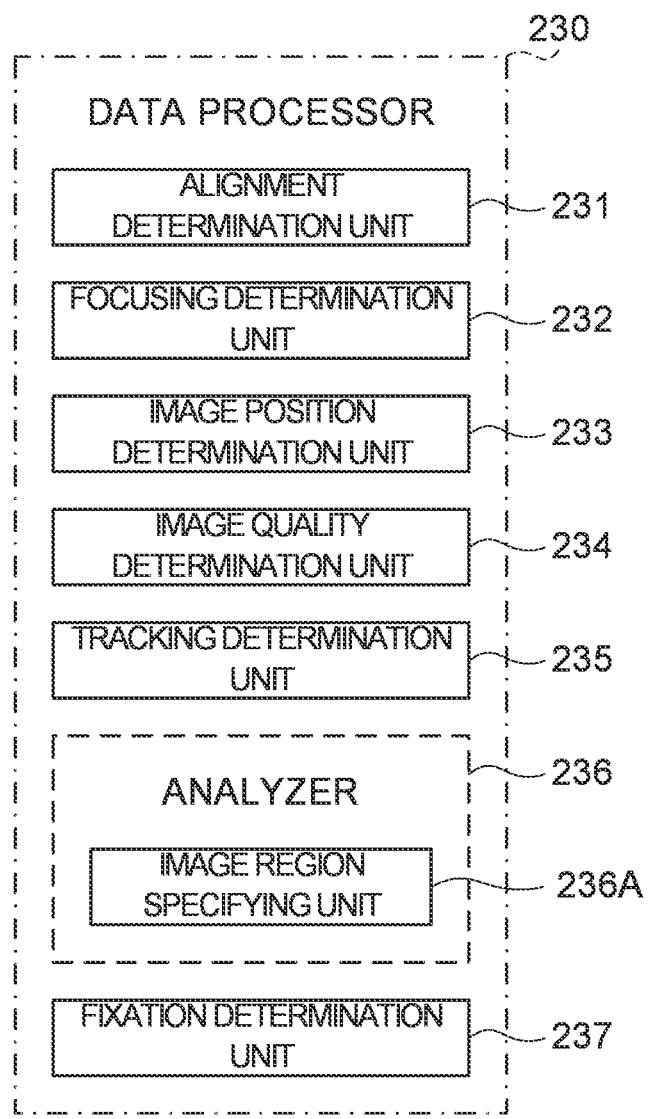
FIG. 4 is a schematic diagram illustrating an example of a configuration of the ophthalmologic apparatus according to the embodiments.

FIGS. 3 and 4 illustrate a configuration example of a control system of the ophthalmologic apparatus 1. In FIGS. 3 and 4, a part of the components included in the ophthalmologic apparatus 1 is omitted. For example, the arithmetic control unit 200 is provided with a controller 210, an image forming unit 220, and a data processor 230.

<Controller 210>

The controller 210 executes various controls. The controller 210 includes a main controller 211 and a storage unit 212.

<Main Controller 211>

The main controller 211 includes a processor and controls each part of the ophthalmologic apparatus 1 (including each element shown in FIGS. 1 to 4). For example, the main controller 211 controls a focusing driver 31A to move the photography focusing lens 31. Furthermore, the main controller 211 controls a focusing driver 43A to move the OCT focusing lens 43. In addition, the main controller 211 controls a reference driver 114A to move the corner cube 114.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction, horizontal direction), a mechanism for moving it in the y direction (up-down direction, vertical direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

In the case of manual alignment, a user operates a user interface (UI) 240 described later to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content on the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the LCD 39. For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 230, for example.

(Storage Unit 212)

The storage unit 212 stores various types of data. Examples of the data stored in the storage unit 212 include data of the subject's eye such as OCT data, OCT images, fundus images, and anterior segment images which are acquired using OCT unit 100, and subject's eye information. The subject's eye information includes information on the subject such as patient ID and name, identification information of the left eye/right eye, information of electronic medical record, and the like.

Further, the storage unit 212 stores fixation position information 212A, determination range information 212B, and message information 212C.

The fixation position information 212A is information representing a fixation position of an eye of a subject (subject's eye E or its fellow eye). The main controller 211 sets a fixation position of the subject's eye E by displaying a fixation target on a screen of the LCD 39 based on the fixation position information 212A. In some embodiments, the fixation position set using the fixation position information 212A is a predetermined position. In some embodiments, the fixation position set using the fixation position information 212A is a predetermined position according to the examination type. In some embodiments, the fixation position set using the fixation position information 212A is a position determined based on the fundus image of the subject acquired in the past without being determined to be in a state of fixation loss. In some embodiments, the fixation position information 212A is a position determined based on an electronic health record of the subject.

The determination range information 212B is information representing a determination range for determining whether or not the subject's eye E is in a state of fixation loss. The main controller 211 causes the data processor 230 to determine whether or not a predetermined site in the fundus Ef of the subject's eye E is included within a determination range based on the determination range information 212B. For example, when it is determined that the predetermined site is not included within the determination range, it can be determined that the subject's eye E is in a state of fixation loss. In some embodiments, the main controller 211 causes the data processor 230 to determine whether or not a predetermined site is included within a determination range in the image of the fundus Ef of the subject's eye E acquired in a state where the fixation light is projected onto the eye of the subject. In some embodiments, a position, a size, and a shape of the determination range set using the determination range information 212B are predetermined. In some embodiments, the determination range information 212B includes information indicating at least one of the position, the size, and the shape of the determination range. In this case, the main controller 211 causes the data processor 230 to determine whether or not a predetermined site in the fundus Ef of the subject's eye E is included within a determination range set based on the determination range information 212B. In some embodiments, a position, a size, and a shape of the determination range set using the determination range information 212B correspond to a fixation position set using the fixation position information 212A. Examples of the predetermined site include an optic disc, a macula, a blood vessel, a lesion, or a scar after treatment.

The message information 212C is information representing a message content for notifying an examiner or the subject of a determination result as to whether or not the subject's eye E is in a state of fixation loss. In some embodiments, the main controller 211 causes the message content corresponding to the determination result described above to be displayed on the LCD 39 or the display unit 240A based on the message information 212C. In some embodiments, the examiner or the subject is made to recognize the determination result described above by stimulating a visual sense, an acoustic sense, a haptic sense, or the like.

<Image Forming Unit 220>

The image forming unit 220 includes a processor and forms an image based on the output from the DAQ 130 (sampling result of the detection signals). For example, the image forming unit 220 forms a reflection intensity profile for each A line by applying signal processing to the spectral distribution on the basis of the sampling detection for each A line in the same manner as in the conventional swept source OCT, images these A line profiles, and arranges them along the scan line. The above signal processing includes noise removal (noise reduction), filtering, fast Fourier transform (FFT), and the like.

<Data Processor 230>

The data processor 230 includes a processor and performs various kinds of image processing and various kinds of analysis processing on the image formed by the image forming unit 220. The data processor 230 includes an alignment determination unit 231, a focusing determination unit 232, an image position determination unit 233, an image quality determination unit 234, a tracking determination unit 235, an analyzer 236, and a fixation determination unit 237. The analyzer 236 includes an image region specifying unit 236A. The auto shoot according to the embodiments can be performed based on the determination result of at least one of the alignment determination unit 231, the focusing determination unit 232, the image position determination unit 233, the image quality determination unit 234, and the tracking determination unit 235.

<Alignment Determination Unit 231>

The alignment determination unit 231 analyzes the image of the fundus Ef of the subject's eye E acquired in a state where the alignment light is projected after alignment adjustment. For example, the alignment determination unit 231 specifies a position (position of the center of gravity, etc.) of an image of an alignment indicator and determines whether or not the specified position is within a predetermined allowable range (alignment scale). When it is determined that the specified position is within the allowable range, the alignment determination unit 231 determines that the alignment state is appropriate. When it is determined that the specified position is not within the allowable range, the alignment determination unit 231 determines that the alignment state is not appropriate. The determination processing in the alignment determination unit 231 is disclosed in, for example, Japanese Unexamined Patent Application Publication No. 2014-039870.

<Focusing Determination Unit 232>

The focusing determination unit 232 determines whether or not the focus state is appropriate, that is, whether or not the fundus Ef is appropriately focused (whether or not it is in focus), at a predetermined timing after the focus adjustment. It should be noted that even after the focus adjustment, such a determination is effective. Because the focus state may change due to the eye movement of the subject's eye E, the movement of the subject, or the like.

The focusing determination unit 232 analyzes the image of the fundus Ef of the subject's eye E acquired in a state where the focus light is projected after focus adjustment. For example, the focusing determination unit 232 specifies positions (position of the center of gravity) in the left-right direction of a pair of acquired split indicator images and determines whether or not the specified position(s) is within an allowable range. This allowable range is set in advance. When it is determined that the specified position is within the allowable range, the focusing determination unit 232 determines that the focus state is appropriate. When it is determined that the specified position is not within the allowable range, the focusing determination unit 232 determines that the focus state is not appropriate. The determination processing in the focusing determination unit 232 is disclosed in, for example, Japanese Unexamined Patent Application Publication No. 2014-039870.

<Image Position Determination Unit 233>

The image position determination unit 233 determines whether or not a position of the tomographic image of the fundus Ef in the frame is appropriate. In particular, the image position determination unit 233 determines whether or not a depth position (position in the z direction) of the tomographic image in the frame is appropriate. The tomographic image is generally acquired after performing alignment adjustment and focus adjustment. Thereby, an image corresponding to the surface of the fundus (surface of the retina) appears in the frame. The image position determination unit 233 specifies the position in the z direction of the image corresponding to this surface of the fundus in the frame. For example, the image position determination unit 233 specifies a pixel corresponding to the surface of the fundus Ef based on the brightness values of the pixel forming the A scan image, and specifies a pixel group arranged along the scanning direction of the measurement light LS. The specified pixel group becomes an image region corresponding to the surface of the fundus Ef. It should be noted that an object to be specified is not limited to the surface of the fundus and the object to be specified may be a site having high-luminance such as IS/OS.

Next, the image position determination unit 233 determines whether or not the specified pixel group is within an allowable range in the z direction. This allowable range is set in advance. When it is determined that the specified pixel group is within the allowable range, the image position determination unit 233 determines that the depth position of the tomographic image in the frame is appropriate. When it is determined that the specified position is not within the allowable range, the image position determination unit 233 determines that the depth position of the tomographic image in the frame is not appropriate.

Alternatively, the determination of the position of the tomographic image may be performed so that the upper end region (image region corresponding to the surface of the fundus) or the lower end region (image region corresponding to the deepest reaching depth of the measurement light LS) of the tomographic image is included in the frame, that is, the upper end region or the lower end region is not gone out of the frame. For example, in each A-scan image, it may be determined whether or not the brightness value in the upper end vicinity region and the lower end vicinity region of the frame is 0, and further whether or not there is a pixel group in which the brightness value is not 0 exists. The determination processing in the image position determination unit 233 is disclosed in, for example, Japanese Unexamined Patent Application Publication No. 2014-039870.

<Image Quality Determination Unit 234>

The image quality determination unit 234 analyzes the tomographic image of the fundus Ef and determines whether or not an image quality of the tomographic image is appropriate. For example, for each A scan image in the depth direction forming the tomographic image, the image quality determination unit 234 specifies the pixel having the maximum luminance and the pixel having the minimum luminance, and generate a histogram of the luminance values based on the luminance values of a pixel group in a predetermined range including the specified pixels (for example, 40 pixels before and after). Next, the image quality determination unit 234 calculates an evaluation value of the image quality from the generated histogram, and determines whether or not the calculated evaluation value is equal to or greater than a predetermined threshold value. This threshold value is set in advance. When the evaluation value is equal to or greater than the threshold value, the image quality determination unit 234 determines that the image quality is appropriate. When the evaluation value is less than the threshold value, the image quality determination unit 234 determines that the image quality is not appropriate. The determination processing in the image quality determination unit 234 is disclosed in, for example, Japanese Unexamined Patent Application Publication No. 2014-039870.

<Tracking Determination Unit 235>

The tracking determination unit 235 determines whether or not the tracking state is appropriate while the tracking (following) of the irradiation position of the measurement light LS with respect to an attention region of the fundus Ef (acquisition target region of the OCT image) is performed. That is, the tracking determination unit 235 determines whether or not the irradiation position of the measurement light LS is appropriately tracked for the eye movement or the like of the subject's eye E.

It should be noted that the tracking can be performed by controlling the optical scanner 42 (galvano mirror). For example, in case of performing tracking based on the fundus image (moving image), the position of the characteristics site (optic disc, etc.) in the fundus is specified in each frame of the moving image, and the irradiation position of the measurement light LS is controlled so that this specified position is always the same position (center region of the frame, etc.).

Alternatively, in case of performing tracking based on the OCT image, a predetermined scan pattern (for example, cross scan) is repeatedly applied, and the irradiation position of the measurement light LS is controlled, based on the characteristic shape (for example, concave shape of the macula) depicted in a pair of tomographic images acquired sequentially, so that the characteristic point (for example, the center of the macula) is always the same position (center region of the frame, etc.).

For example, the tracking determination unit 235 determines whether or not the tracking state is appropriate by determining whether or not a tracking target site is within a scan region of the measurement light LS. The scan region is set in, for example, a predetermined region (6 mm×6 mm square area or the like) centered on the optical axis of the imaging optical system 30.

<Analyzer 236>

The analyzer 236 analyzes the data acquired by OCT scan using the OCT unit 100 or the image acquired using the imaging optical system 30. In particular, the analyzer 236 analyzes the image of the fundus Ef of the subject's eye E acquired in a state where the fixation light is projected onto the eye of the subject, and specifies a region corresponding to a predetermined site of the fundus Ef of the subject's eye E. The predetermined site of the fundus Ef of the subject's eye E may be arbitrary. For example, the predetermined site may be an optic disc, a macula, a lesion, a blood vessel of interest, or the like.

<Image Region Specifying Unit 236A>

The image region specifying unit 236A specifies a rectangular area circumscribing a predetermined site such as an optic disc based on a luminance value of a pixel or a representative luminance value of a plurality pixel blocks of the image of the fundus Ef of the subject's eye, the image being acquired in a state where the fixation light is projected onto the eye of the subject. It should be noted that the shape of the region specified by the image region specifying unit 236A is not limited to a rectangle.

Alternatively, the image region specifying unit 236A may obtain a luminance distribution based on a luminance value of a pixel or a representative luminance value of a plurality pixel blocks of the image of the fundus Ef of the subject's eye, the image being acquired in a state where the fixation light is projected onto the eye of the subject, and may specify one or more candidate regions from the obtained luminance distribution. In this case, the image region specifying unit 236A specify an image region corresponding to a desired predetermined site from the shape or the size of each specified candidate region, relative positional relationship, size relationship, or shape relationship to other candidate regions, etc. The image of the fundus Ef is an image of the fundus Ef acquired using the imaging optical system 30. The image of the fundus Ef may be a front image of the fundus Ef formed based on the data acquired by performing OCT scan using the OCT unit 100. Examples of the front image of the fundus Ef include a C scan image, a shadowgram, a projection image, and the like. In the case that the ophthalmologic apparatus 1 includes a SLO optical system, the image of the fundus Ef may be a front image of the fundus obtained using the SLO optical system.

<Fixation Determination Unit 237>

The fixation determination unit 237 determines whether or not the image region specified by the image region specifying unit 236A is included within a predetermined range in the acquired image of the fundus Ef. The predetermined range is set using the determination range information 212B. The fixation determination unit 237 determines that the image region described above is included within the determination range set based on the determination range information 212B, when the entire image region specified by the image region specifying unit 236A is included within the predetermined range in the image of the fundus Ef. The fixation determination unit 237 determines that the image region described above is not included within the determination range set based on the determination range information 212B, when at least part of the image region specified by the image region specifying unit 236A is not included within the predetermined range in the image of the fundus Ef.

Alternatively, the fixation determination unit 237 may determine that the image region described above is included within the determination range set based on the determination range information 212B, when at least part of the image region specified by the image region specifying unit 236A is included within the predetermined range in the image of the fundus Ef. In the same way, the fixation determination unit 237 may determine that the image region described above is not included within the determination range set based on the determination range information 212B, when the entire image region specified by the image region specifying unit 236A is not included within the predetermined range in the image of the fundus Ef.

The controller 210 causes the fixation determination unit 237 to determine whether the subject's eye E is in a state of fixation loss, in the case that the determination results of the alignment determination unit 231, the focusing determination unit 232, the image position determination unit 233, the image quality determination unit 234, and the tracking determination unit 235 are all appropriate. When it is determined by the fixation determination unit 237 that the subject's eye E is not in a state of fixation loss, the controller 210 starts OCT measurement using the OCT unit 100 or starts image acquisition of the fundus Ef using the imaging optical system 30.

In some embodiments, when it is determined by the fixation determination unit 237 that the subject's eye E is not in a state of fixation loss, the controller 210 starts OCT measurement or image acquisition after notifying that the subject's eye E is not a state of the fixation loss. For example, the notification is realized by displaying a message on the LCD 39 or the display unit 240A.

In some embodiments, when it is determined by the fixation determination unit 237 that the subject's eye E is in a state of fixation loss, the controller 210 notifies that the subject's eye E is in a state of fixation loss. For example, the notification is realized by displaying a message on the LCD 39 or the display unit 240A.

In some embodiments, when it is determined by the fixation determination unit 237 that the subject's eye E is in a state of fixation loss, the controller 210 causes information for guiding a fixation position of the subject's eye E to a predetermined fixation position to be displayed on the LCD 39 or the display unit 240A after notifying that the subject's eye E is in a state of fixation loss. Examples of the information for guiding the fixation position of the subject's eye E to the predetermined fixation position include characters, arrows, and the like that indicate the direction to which the fixation position should move and the amount of movement. The fixation position of the subject's eye E may be guided to the predetermined fixation position using audio output.

In some embodiments, when it is determined by the fixation determination unit 237 that the subject's eye E is in a state of fixation loss, the controller 210 changes the projection position of the fixation light so as to guide the fixation position of the subject's eye E to the predetermined fixation position by controlling the LCD 39.

In some embodiments, when it is determined by the fixation determination unit 237 that the subject's eye E is in a state of fixation loss, the controller 210 may switch the operation mode. For example, the controller 210 switches the operation mode of the auto shoot (auto shoot mode) to the operation mode of the manual shoot (manual shoot mode). In the operation mode of the manual shoot, the controller 210 controls the moving mechanism 150 based on the operation content on the user interface 240 by the user to perform the manual alignment. After that, OCT measurement or image acquisition is started based on the operation content on the user interface 240 by the user.

<User Interface 240>

The user interface 240 includes the display unit 240A and an operation unit 240B. The display unit 240A includes a display apparatus 3. The operation unit 240B includes various operation devices and input devices.

The user interface 240 may include a device having the output function and the input function integrated together, such as a touch panel display, for example. In another embodiment, at least a part of the user interface 240 may not be included in the ophthalmologic apparatus. For example, the display device may be an external device connected to the ophthalmologic apparatus.

For example, the optical system from the LCD 39 to the objective lens 22 in FIG. 1 is an example of the "fixation system" according to the embodiments. For example, the imaging optical system 30 or the optical system form the OCT unit 100 to the objective lens 22 is an example of the "image acquisition unit" according to the embodiments. For example, the image region specifying unit 236A is an example of the "specifying unit" according to the embodiments. For example, the fixation determination unit 237 is an example of the "determination unit" according to the embodiments. For example, the imaging optical system 30 or the optical system form the OCT unit 100 to the objective lens 22 is an example of the "data acquisition unit" according to the embodiments. For example, the LCD 39 or the display unit 240A is an example of the "notifying unit" according to the embodiments. For example, the LCD 39 or the display unit 240A is an example of the "display unit" according to the embodiments. For example, the user interface 240 or the operation unit 240B is an example of the "operation unit" according to the embodiments.

<Operation>

An operation example of the ophthalmologic apparatus 1 will be described.

Figure 5:
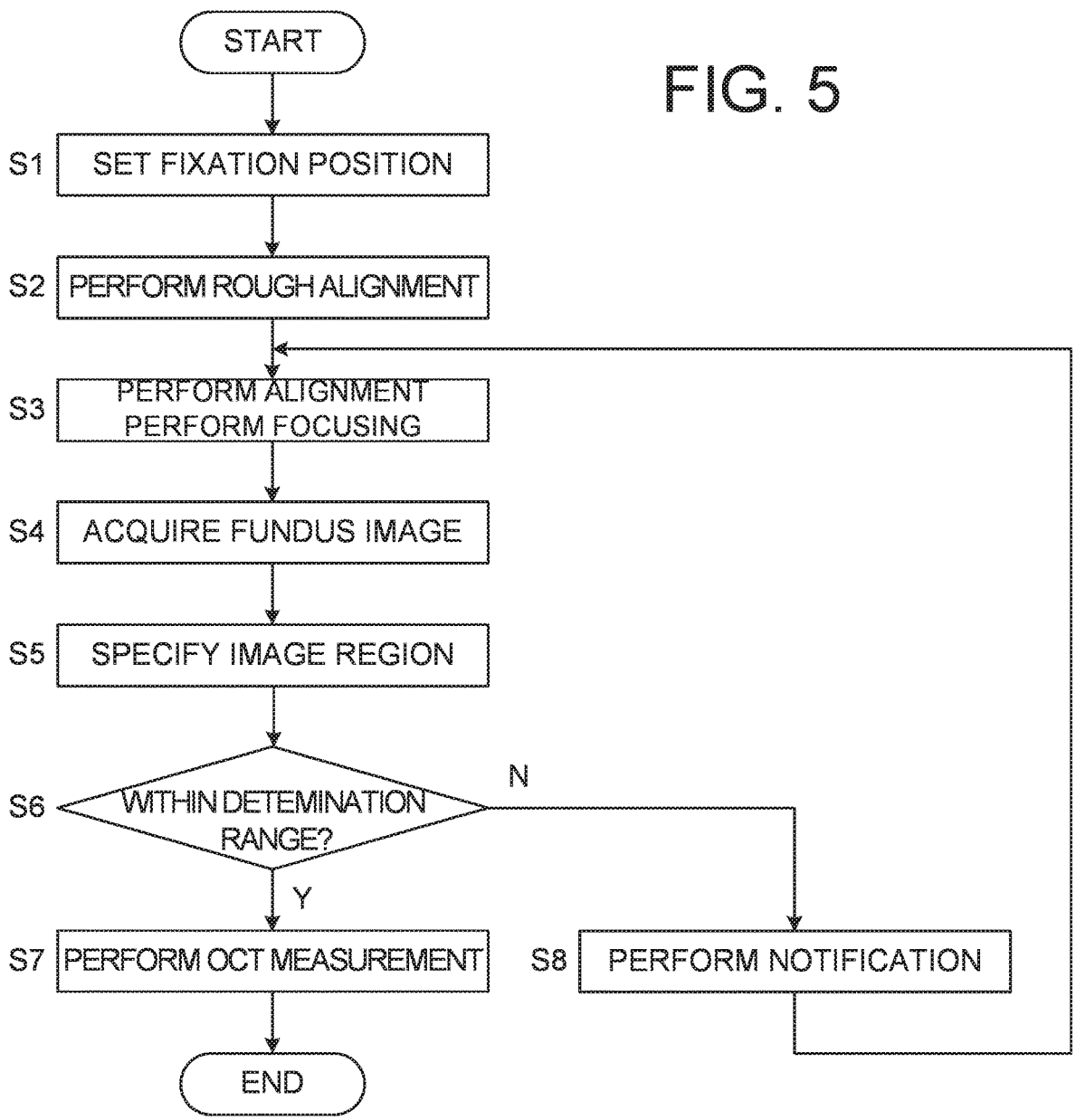
FIG. 5 is a schematic diagram illustrating an example of an operation of the ophthalmologic apparatus according to the embodiments.

FIG. 5 shows an example of the operation of the ophthalmologic apparatus 1 according to the embodiments. FIG. 5 shows a flow of an operation example in the case that the operation mode is preset to the auto shoot mode and it is determined whether or not the subject's eye E is in a state of fixation loss after the completion of the automatic alignment and the automatic focus.

(S1: Set Fixation Position)

First, the fixation position is designated. The fixation position is designated manually or automatically. In case of designating manually, the main controller 211 causes GUI for designating the fixation position to be displayed on the display unit 240A. The user sets a desired fixation position using this GUI and the operation unit 240B. In case of designating automatically, the main controller 211 designates the fixation position based on the fixation position information 212A or information input from external. Examples of the information input from external include electronic health record of the subject input from the electronic health record system, shoot mode designated manually or automatically, and the like.

The main controller 211 controls the LCD 39 so as to display a fixation target at a position corresponding to the designated fixation position. Thereby, the fixation light is projected onto the subject's eye E. The fixation light is continuously projected onto the subject's eye E until the OCT measurement or the image acquisition is completed, for example.

(S2: Perform Rough Alignment)

The controller 210 performs rough alignment. For example, the main controller 211 obtains the three-dimensional relative position between the optical system and the subject's eye E using a known method, by analyzing two anterior segment images acquired substantially simultaneously from different directions by the anterior segment cameras 5A and 5B to specify a pupil region in each anterior segment image. The main controller 211 relatively moves the optical system and the subject's eye E by controlling the movement mechanism 150 so as to cancel the displacement of the subject's eye E with respect to the optical system, based on the obtained three-dimensional relative position. The main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance.

(S3: Perform Alignment, Perform Focusing)

Next, the controller 210 controls each part of the ophthalmologic apparatus 1 so that the determination results of the alignment determination unit 231, the focusing determination unit 232, the image position determination unit 233, the image quality determination unit 234, and the tracking determination unit 235 are all appropriate. For example, the main controller 211 controls the alignment optical system 50 so as to project the alignment light onto the subject's eye E and controls the focus optical system 60 so as to project the focus light onto the subject's eye E. Further, the main controller 211 performs automatic alignment and automatic focus as is conventionally done. Thereby, alignment and focusing for the fundus Ef are completed.

(S4: Acquire Fundus Image)

The controller 210 controls the illumination optical system 10 and the imaging optical system 30 so as to start image acquisition of the fundus Ef of the subject's eye E. For example, the acquired image is an image (moving image) acquired by photographing the fundus Ef of the subject's eye E from the front.

(S5: Specify Image Region)

The controller 210 causes the image region specifying unit 236A to specify the image region corresponding to an optic disc in the image of the fundus Ef of the subject's eye acquired in step S4.

(S6: Within Determination Range?)

Next, the controller 210 causes the fixation determination unit 237 to determine whether or not the image region specified in step S5 is included within the determination range designated using the determination range information 212B.

Figure 6:
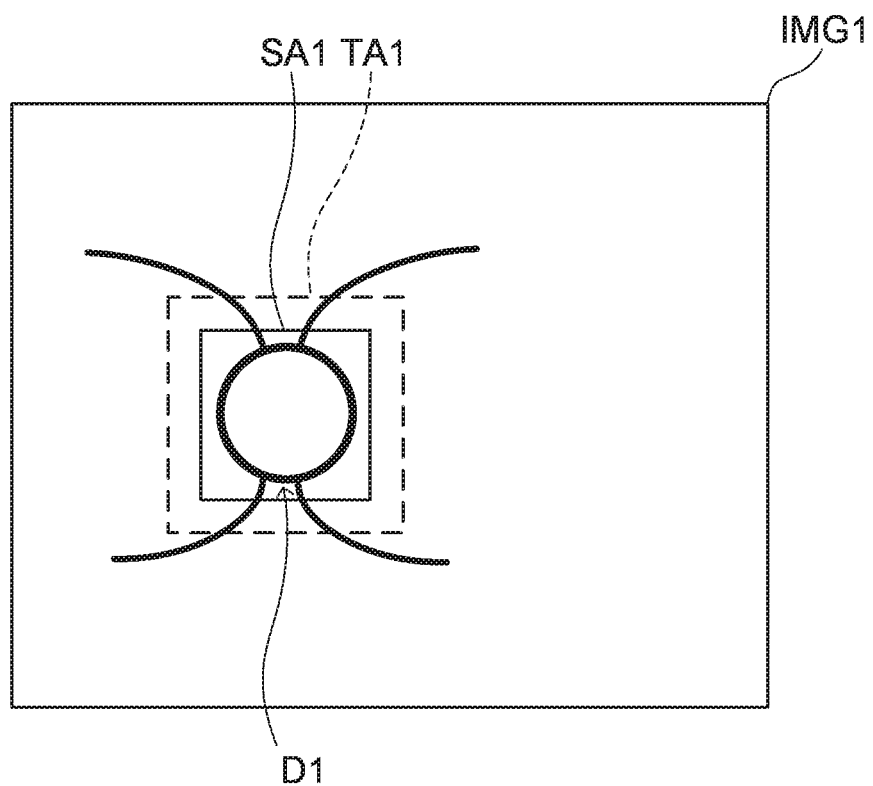
FIG. 6 is a schematic diagram for explaining the operation of the ophthalmologic apparatus according to the embodiments.

For example, in step S5, as shown in FIG. 6, it is assumed that the image region SA1 corresponding to the optic disc D1 is specified in the image IMG1 of the fundus Ef. When the entire image region SA1 is included within the determination range TA1 in the image IMG1, the fixation determination unit 237 determines that the subject's eye E is not in a state of fixation loss.

Figure 7:
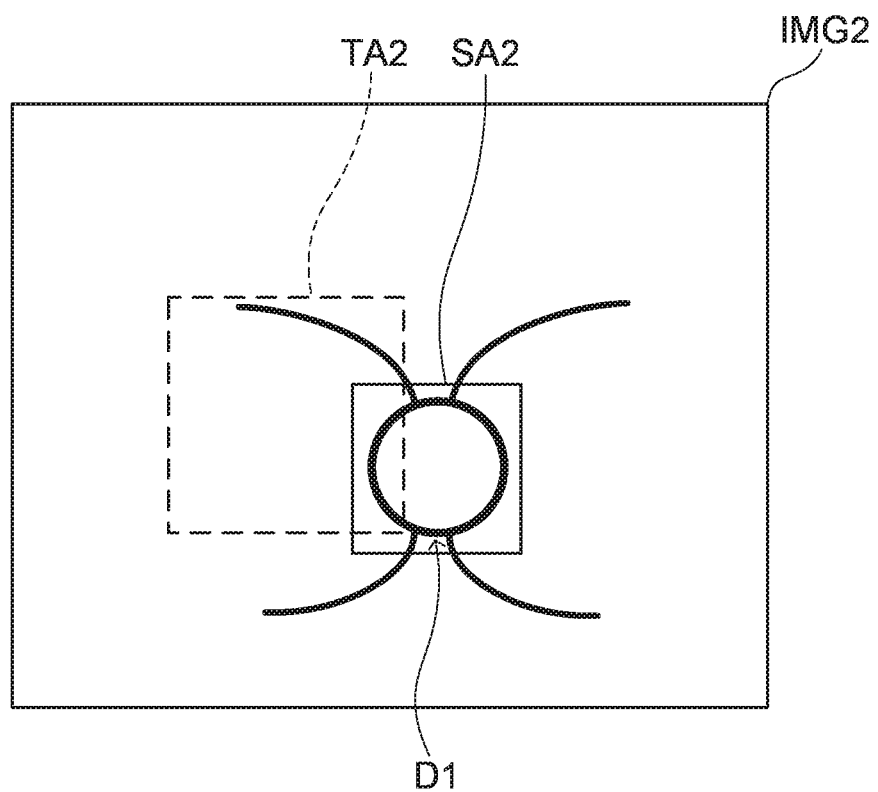
FIG. 7 is a schematic diagram for explaining the operation of the ophthalmologic apparatus according to the embodiments.

For example, in step S5, as shown in FIG. 7, it is assumed that the image region SA2 corresponding to the optic disc D1 is specified in the image IMG2 of the fundus Ef. When the entire image region SA2 is not included within the determination range TA2 in the image IMG2, the fixation determination unit 237 determines that the subject's eye E is a state of the fixation loss.

When it is determined by the fixation determination unit 237 that the image region specified in step S5 is included within the determination range (S6: Y), the operation of the ophthalmologic apparatus 1 proceeds to step S7. When it is determined by the fixation determination unit 237 that the image region specified in step S5 is not included within the determination range (S6: N), the operation of the ophthalmologic apparatus 1 proceeds to step S8.

(S7: Perform OCT Measurement)

When it is determined that the image region specified in step S5 is included within the determination range in step S6 (S6: Y), the controller 210 controls the optical scanner 42 and the OCT unit 100 so as to start performing OCT measurement. When the OCT measurement is started, the OCT unit 100 sends data collected for each scan to the image forming unit 220. The image forming unit 220 forms a plurality of B scan images from the data collected for each scan and sends them to the controller 210. The controller 210 sends the plurality of B scan images corresponding to each scan to the data processor 230. For example, the data processor 230 forms a three-dimensional image from the plurality of B scan images corresponding to each scan. This terminates the operation of the ophthalmologic apparatus 1 (END).

(S8: Perform Notification)

When it is determined that the image region specified in step S5 is not included within the determination range in step S6 (S6: N), the controller 210 performs notification that the subject's eye E is in a state of fixation loss. For example, the controller 210 causes the message content indicating that the subject's eye E is in a state of fixation loss to be displayed on the LCD 39 or the display unit 240A.

In some embodiments, in any one of step S5 to step S8, the controller 210 causes the acquired image of the fundus Ef of the subject's eye E to be displayed on the LCD 39 or the display unit 240A. Further, the controller 210 causes information representing the determination range or the image region specified in step S5 to be superimposed on the image of the fundus Ef and to be displayed. Examples of the information representing the determination range or the image region include a position information representing the determination range or the image region, an image representing the determination range or the image region (image representing a frame), and the like. In this case, in step S8, the controller 210 can notify that the subject's eye E is in a state of fixation loss by blinking the position information representing the determination range or the image region or the image representing the determination range or the image region.

When step S8 is terminates, the operation of the ophthalmologic apparatus 1 proceeds to step S3.

Figure 8:
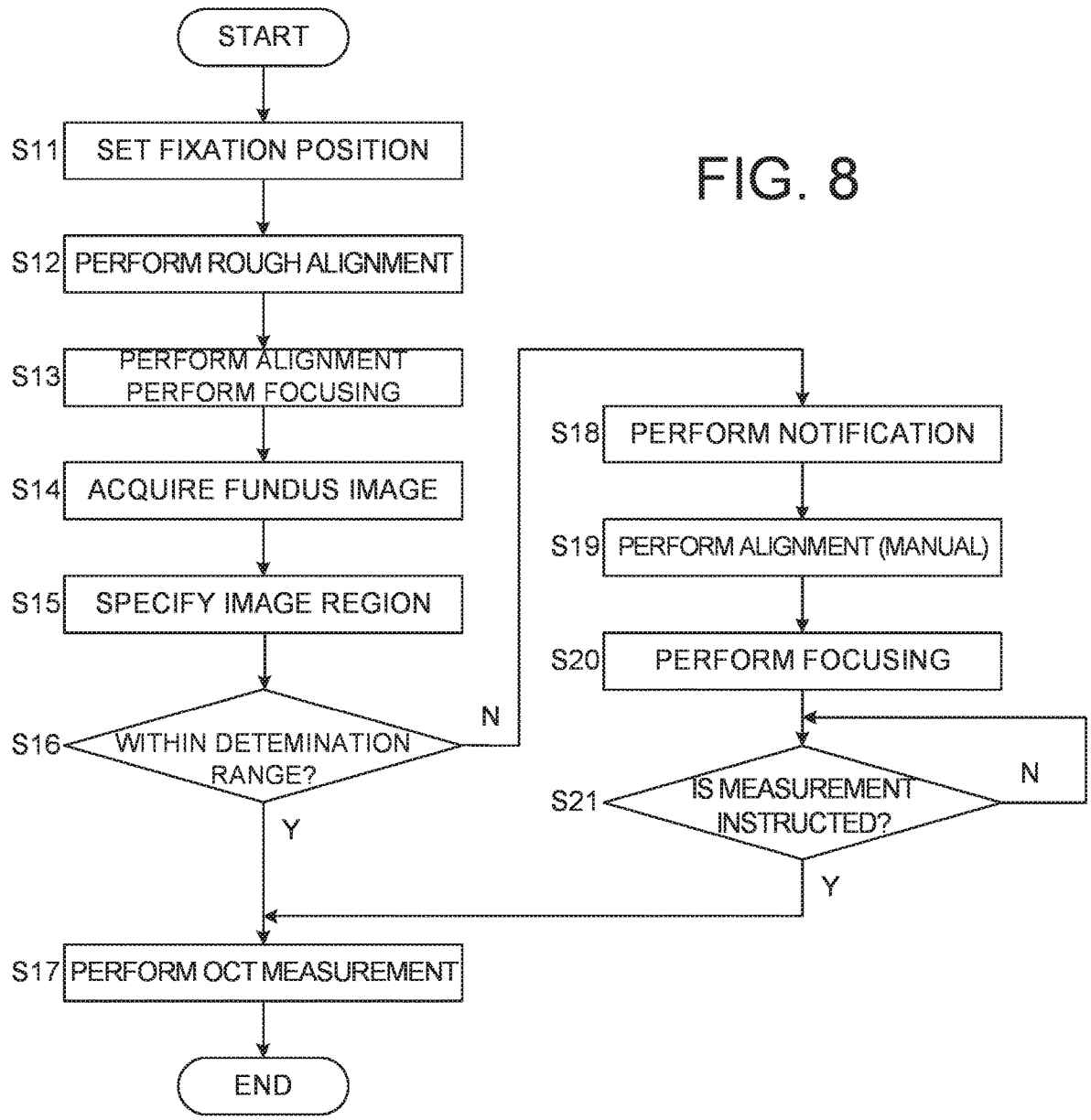
FIG. 8 is a schematic diagram illustrating an example of a configuration of the ophthalmologic apparatus according to the embodiments.

FIG. 8 shows an example of another operation of the ophthalmologic apparatus 1 according to the embodiments. FIG. 8 shows a flow of an operation example in the case that the operation mode is preset to the auto shoot mode, and when it is determined that the subject's eye E is in a state of fixation loss after the completion of the automatic alignment and the automatic focus, the operation mode proceeds to the manual shoot mode.

(S11: Set Fixation Position)

In step S11, the fixation position is set in the same manner as step S1. The main controller 211 controls the LCD 39 so as to display a fixation target at a position corresponding to the designated fixation position. Thereby, the fixation light is projected onto the subject's eye E. The fixation light is continuously projected onto the subject's eye E until the OCT measurement or the image acquisition is completed, for example.

(S12: Perform Rough Alignment)

The controller 210 performs schematic alignment, in the same manner as step S2.

(S13: Perform Alignment, Perform Focusing)

Next, in the same manner as step S3, the controller 210 controls each part of the ophthalmologic apparatus 1 so that the determination results of the alignment determination unit 231, the focusing determination unit 232, the image position determination unit 233, the image quality determination unit 234, and the tracking determination unit 235 are all appropriate.

(S14: Acquire Fundus Image)

In the same manner as step S4, the controller 210 controls the illumination optical system 10 and the imaging optical system 30 so as to start image acquisition of the fundus Ef of the subject's eye E.

(S15: Specify Image Region)

In the same manner as step S5, the controller 210 causes the image region specifying unit 236A to specify the image region corresponding to an optic disc in the image of the fundus Ef of the subject's eye acquired in step S14.

(S16: Within Determination Range?)

Next, in the same manner as step S6, the controller 210 causes the fixation determination unit 237 to determine whether or not the image region specified in step S15 is included within the determination range designated using the determination range information 212B.

When it is determined by the fixation determination unit 237 that the image region specified in step S15 is included within the determination range (S16: Y), the operation of the ophthalmologic apparatus 1 proceeds to step S17. When it is determined by the fixation determination unit 237 that the image region specified in step S15 is not included within the determination range (S16: N), the operation of the ophthalmologic apparatus 1 proceeds to step S18.

(S17: Perform OCT Measurement)

When it is determined that the image region specified in step S15 is included within the determination range in step S16 (S16: Y), the controller 210 controls the optical scanner 42 and the OCT unit 100 so as to start performing OCT measurement, in the same manner as step S7. This terminates the operation of the ophthalmologic apparatus 1 (END).

(S18: Perform Notification)

When it is determined that the image region specified in step S15 is not included within the determination range in step S16 (S16: N), the controller 210 switches the operation mode to the manual shoot mode. Further, the controller 210 notifies that the subject's eye E is in a state of fixation loss, in the same manner as step S8. For example, the controller 210 causes the message content indicating that the subject's eye E is in a state of fixation loss to be displayed on the LCD 39 or the display unit 240A.

(S19: Perform Alignment)

Subsequently, the controller 210 performs manual alignment. For example, the main controller 211 controls the alignment optical system 50 so as to project the alignment light onto the subject's eye E. The main controller 211 causes an alignment indicator image on the basis of return light of the alignment light and an alignment mark representing the allowable range of the alignment to be displayed on a display screen of the display unit 240A. The user operates the user interface 240 so that the alignment indicator image enters within the alignment mark. The main controller 211 controls the movement mechanism 150 to relatively move the optical system and the subject's eye E by outputting a control signal corresponding to the operation content on the user interface 240 by the user to the movement mechanism 150.

(S20: Perform Focusing)

Next, the controller 210 performs focusing. For example, the main controller 211 controls the focus optical system 60 so as to project the focus light onto the subject's eye E. The main controller 211 causes a pair of split indicator images to be displayed on the display screen of the display unit 240A. The user operates the user interface 240 so that the pair of split indicator images enters within the allowable range. The main controller 211 controls the photography focusing lens 31 and the OCT focusing lens 43 to move in the optical axis direction by outputting a control signal corresponding to the operation content on the user interface 240 by the user to the focusing drivers 31A and 43A.

It should be noted that the automatic focus may be performed in the same manner as step S13, in step S20.

(S21: Is Measurement Instructed?)

Next, the controller 210 monitors whether or not there is an instruction for OCT measurement (S21: N). For example, the user can instruct to start OCT measurement by performing a predetermined operation on the user interface 240. The controller 210 determines whether or not there is an instruction for OCT measurement based on the operation content on the user interface 240. When it is determined that there is an instruction for OCT measurement (S21: Y), the operation of the ophthalmologic apparatus 1 proceeds to step S17.

It should be noted that noted that, in step S6 of FIG. 5 or step S16 of FIG. 8, when it is determined that the specified image region is included within the determination range, the controller 210 may notify that the measurement is to be started (that is, the subject's eye E is not in a state of fixation loss). For example, the controller 210 starts the OCT measurement, after causing the message content indicating that the measurement is to be started to be displayed on the LCD 39 or the display unit 240A.

Figure 9:
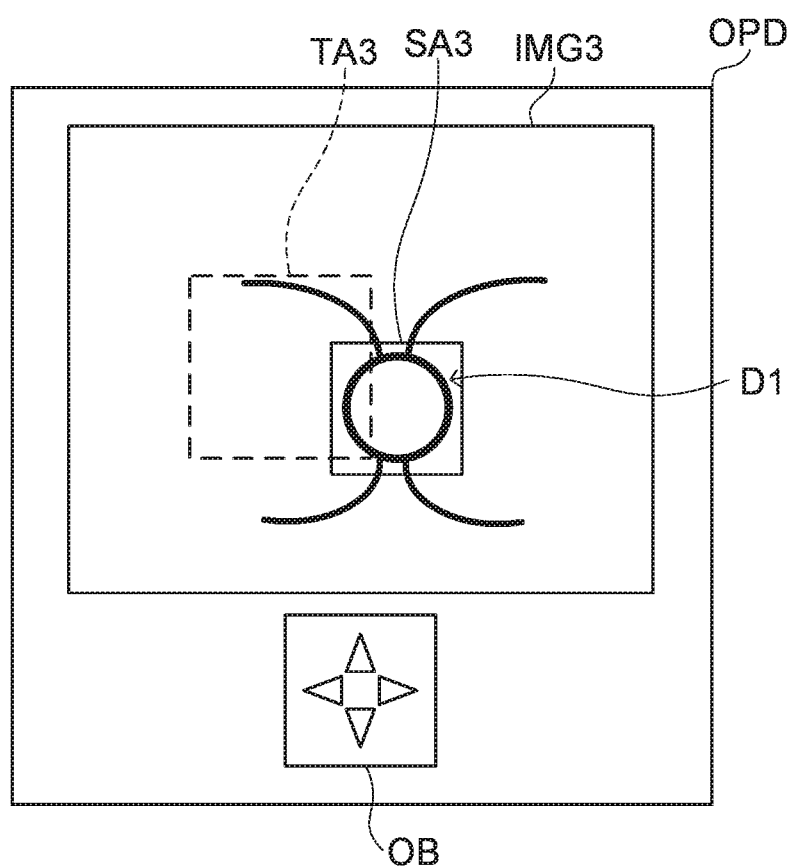
FIG. 9 is a schematic diagram for explaining the operation of the ophthalmologic apparatus according to a modification example of the embodiments.

Alternatively, in step S6 of FIG. 5 or step S16 of FIG. 8, when it is determined that the specified image region is not included within the determination range, the controller 210 may cause a fixation position adjustment operation object to be displayed on the display unit 240A after notifying that the subject's eye E is in a state of fixation loss. For example, as shown in FIG. 9, the operation screen OPD is displayed on the display unit 240A. The image IMG3 of the fundus Ef and the fixation position adjustment operation object OB are displayed on the operation screen OPD. In the image IMG3, an image representing the image region SA3 corresponding to the optic disc D1 and an image representing the determination range TA3 are depicted. In this case, when it is determined that the subject's eye E is in a state of fixation loss, the controller 210 starts the countdown of the measurement start, and prompts the user to perform a touch operation on the fixation position adjustment operation object OB. The controller 210 changes the fixation position by controlling the LCD 39 based on a control signal corresponding to a touch operation content on the fixation position adjustment operation object OB during countdown of the measurement start.

It should be noted that when it is determined that the subject's eye E is in a state of fixation loss, the controller 210 may prompt the user perform a touch operation on the fixation position adjustment operation object OB, without starting the countdown of the measurement start.

<Modification Example 1>

In the above embodiments, the case has been described in which the fixation determination unit 237 determines whether the subject's eye E is in a state of fixation loss, in the auto shoot mode; however, the configuration according to the embodiments is not limited thereto. For example, the fixation determination unit 237 may whether the subject's eye E is in a state of fixation loss, in the manual shoot mode. In this case, in the manual shoot mode, the image region specifying unit 236A analyzes the image of the fundus Ef of the subject's eye E on which the fixation light is projected, the image being acquired at an arbitrary timing, and specifies the image region corresponding to a predetermined site in the fundus Ef. The fixation determination unit 237 determines whether or not the image region is included within a predetermined range. The controller 210 cause a notification unit to notify based on the determination result obtained by the fixation determination unit 237.

<Modification Example 2>

In the embodiments described above, the case has been described in which the notification corresponding to the determination result obtained by the fixation determination unit 237 is performed; however, the configuration according to the embodiments is not limited thereto. For example, the controller 210 may store the OCT data acquired using the OCT unit 100 or the image acquired using the imaging optical system 30 in storage unit 212 in association with the information corresponding to the determination result obtained by the fixation determination unit 237. For example, the acquired OCT data or the image is associated with the information that the subject's eye E to be acquired is in a state of fixation loss or the information that the subject's eye E to be acquired is not in a state of fixation loss. The measurement is interrupted by the notification when it is determined that the subject's eye E is in a state of fixation loss. In this case, it is possible to prevent the measurement time from becoming long due to this interruption.

<Actions and Effects>

Described below are the actions and effects of the ophthalmologic apparatus according to the embodiments.

An ophthalmologic apparatus (1) according to the embodiments acquires data of a fundus (Ef) of a subject's eye (E) optically. The ophthalmologic apparatus includes a fixation system (optical system from the LCD 39 to the objective lens 22), an image acquisition unit (imaging optical system 30, or optical system from the OCT unit 100 to the objective lens 22), a specifying unit (image region specifying unit 236A), and a determination unit (fixation determination unit 237). The fixation system is configured to project fixation light onto an eye of a subject. The image acquisition unit is configured to acquire an image of the fundus of the subject's eye in a state where the fixation light is projected by the fixation system. The specifying unit is configured to analyze the image acquired by the image acquisition unit to specify an image region corresponding to a predetermined site of the fundus. The determination unit is configured to determine whether or not the image region specified by the specifying unit is included within a predetermined range (determination range) in the image acquired by the image acquisition unit.

For example, the fixation system projects the fixation light from an internal fixation light source or an external fixation light source. For example, the eye of the subject is the subject's eye in case of projecting the fixation light from the internal fixation light source, and the eye of the subject is the fellow eye in case of projecting the fixation light from the external fixation light source. For example, the image of the fundus is a front image of the fundus acquired using the imaging optical system, a front image of the fundus acquired using SLO, a C scan image acquired using OCT, a shadowgram, or a projection image. For example, the predetermined site of the fundus is an optic disc, a macula, a blood vessel, a lesion, or a scar after treatment.

According to such a configuration, whether the subject's eye is in a state of fixation loss can be determined, by analyzing the image of the fundus of the subject's eye acquired in a state where the fixation light is projected onto the subject's eye and determining whether or not the image region in the predetermined site of the fundus is included within the predetermined range. Thereby, the ophthalmologic apparatus capable of appropriately dealing with fixation loss can be provided, by operating the ophthalmologic apparatus according to the determination result of whether or not the subject's eye is in a state of fixation loss.

The ophthalmologic apparatus according to the embodiments may include a data acquisition unit (imaging optical system 30, or optical system from the OCT unit 100 to the objective lens 22) and a controller (210). The data acquisition unit is configured to optically acquire the data. The controller is configured to cause the data acquisition unit to acquire the data when it is determined by the determination unit that the image region is included within the predetermined range.

According to such a configuration, it can be determined that the subject's eye is not in a state of fixation loss when it is determined that the image region corresponding to the predetermined site of the fundus is included within the predetermined range. Thereby, the ophthalmologic apparatus capable of reliably acquired data of a desired site in the fundus can be provided.

The ophthalmologic apparatus according to the embodiments may include a movement mechanism (150). The movement mechanism is configured to change relative position between the subject's eye and the data acquisition unit. The controller is configured: to perform alignment between the subject's eye and the data acquisition unit by controlling the movement mechanism; to cause the image acquisition unit to acquire the image after the alignment is completed; and; to cause the data acquisition unit to acquire the data when it is determined by the determination unit that the image region is included within the predetermined range.

According to such a configuration, whether or not the subject's eye is in a state of fixation loss can be determined after the alignment is completed. Thereby, in the operation mode (for example, auto shoot mode) in which the acquisition of data is automatically started after the alignment is completed, prolonged examination time due to reacquisition of the data due to the fixation loss of the subject's eye can be prevented.

The ophthalmologic apparatus according to the embodiments may include a notification unit (LCD 39 or display unit 240A). The notification unit is configured to perform notification corresponding to a determination result obtained by the determination unit. The controller is configured to cause the notification unit to notify based on the determination result obtained by the determination unit.

According to such a configuration, for example, when it is determined that the subject's eye is in a state of fixation loss, the examiner or the subject can be notified that data of the desired site can not be acquired, before acquiring data. Further, for example, when it is determined that the subject's eye is not in a state of fixation loss, the examiner or the subject can be notified that data of the desired site can be acquired, before acquiring data. Therefore, the ophthalmologic apparatus capable of appropriately dealing with the determination result of whether the subject's eye is in a state of fixation loss can be provided.

The ophthalmologic apparatus according to the embodiments may include an operation unit (user interface 240 or operation unit 240B) and a notification unit (LCD 39 or display unit 240A). The notification unit is configured to perform notification corresponding to a determination result obtained by the determination unit. The controller is configured to cause the notification unit to perform notification and to control the movement mechanism based on an operation content on the operation unit, when it is determined by the determination unit that the image region is not included within the predetermined range.

According to such a configuration, when it is determined that the subject's eye is in a state of fixation loss, the movement mechanism can be controlled according to the operation content on the operation unit after notification. Thereby, the examiner or the subject can adjust the fixation position, or the like.

In the ophthalmologic apparatus according to the embodiments, the notification unit may include a display unit (LCD 39 or display unit 240A). The controller is configured to cause a message content corresponding to the determination result obtained by the determination unit to be displayed on the display unit.

According to such a configuration, the notification can be performed by causing the message content corresponding to the determination result obtained by the determination unit to be displayed. Thereby, the examiner or the subject can recognize whether or not the subject's eye is in a state of fixation loss, before acquiring data.

In the ophthalmologic apparatus according to the embodiments, the notification unit may include a display unit (LCD 39 or display unit 240A). The controller is configured: to cause the image acquired by the image acquisition unit to be displayed on the display unit and to cause information representing the predetermined range or the image region to be displayed so as to be superimposed on the image; and to blink the information when it is determined by the determination unit that the image region is not included within the predetermined range.

According to such a configuration, when it is determined that the subject's eye is in a state of fixation loss, the information representing the predetermined range or the image region displayed so as to be overlaid on the image of the fundus can be blinked. Thereby, the examiner or the subject can recognize whether or not the subject's eye is in a state of fixation loss, before acquiring data.

The ophthalmologic apparatus according to the embodiments may include a display unit (LCD 39 or display unit 240A). The controller is configured to cause information for guiding a fixation position of the subject's eye to a predetermined fixation position to be displayed on the display unit.

According to such a configuration, when it is determined that the subject's eye is in a state of fixation loss, the fixation position of the subject's eye is guided to the predetermined fixation position. Thereby, it becomes possible to easily adjust to a desired fixation state before data acquisition.

The ophthalmologic apparatus according to the embodiments may include a data acquisition unit (imaging optical system 30, or optical system from the OCT unit 100 to the objective lens 22) and a controller (210). The data acquisition unit is configured to optically acquire the data. The controller is configured to cause the data acquisition unit to acquire the data and to store the data in a storage unit (212) in association with information corresponding to a determination result obtained by the determination unit.

According to such a configuration, the data of the subject's eye can be acquired by the data acquisition unit without notification corresponding to the determination result obtained by the determination unit. Thereby, whether or not the data is acquired in the desired fixation state based on the associated information can be determined. Therefore, an ophthalmologic apparatus capable of acquiring data in the desired fixation state while shortening the examination time can be provided.

In the ophthalmologic apparatus according to the embodiments, the controller may be configured to change a projection position of the fixation light so as to guide a fixation position of the subject's eye to a predetermined fixation position by controlling the fixation system, when it is determined by the determination unit that the image region is not included within the predetermined range.

According to such a configuration, when it is determined that the subject's eye is in a state of fixation loss, the fixation position of the subject's eye is guided to the predetermined fixation position by changing the projection position of the fixation light. Thereby, it becomes possible to easily adjust to a desired fixation state before data acquisition.

In the ophthalmologic apparatus according to the embodiments, the predetermined range may be able to be set according to the subject's eye.

According to such a configuration, the data can be acquired in a fixation state suitable for the subject's eye.

In the ophthalmologic apparatus according to the embodiments, the predetermined site may be an optic disc, a macular region, a blood vessel, a lesion, or a scar after treatment.

According to such a configuration, the accuracy of determining whether or not the subject's eye is in a state of fixation loss can be improved.

A method of controlling an ophthalmologic apparatus (1) is a method of controlling the ophthalmologic apparatus acquiring data of a fundus (Ef) of a subject's eye (E) optically. This method includes projecting fixation light onto an eye of a subject using a fixation system (optical system from LCD 39 to objective lens 22); acquiring an image of the fundus of the subject's eye in a state where the fixation light is projected by the fixation system; analyzing the acquired image to specify an image region corresponding to a predetermined site of the fundus; and determining whether or not the specified image region is included within a predetermined range in the acquired image.

According to such a configuration, whether the subject's eye is in a state of fixation loss can be determined, by analyzing the image of the fundus of the subject's eye acquired in a state where the fixation light is projected onto the subject's eye and determining whether or not the image region in the predetermined site of the fundus is included within the predetermined range. Thereby, the ophthalmologic apparatus capable of appropriately dealing with fixation loss can be provided, by operating the ophthalmologic apparatus according to the determination result of whether or not the subject's eye is in a state of fixation loss.

The method of controlling the ophthalmologic apparatus according to the embodiments may include performing notification when it is determined that the image region is not included within the predetermined range.

In the method of controlling the ophthalmologic apparatus according to the embodiments, the data may be acquired when it is determined that the image region is included within the predetermined range.

The embodiments described above are merely examples. One who intends to implement the present invention may arbitrarily modify (omission, replacement, addition, etc.) within the scope of the invention.

A program for causing a computer to execute the method of controlling the ophthalmologic apparatus according to the embodiments is stored in the storage unit 212. Such a program can be stored in any kind of recording medium that can be read by the computer. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ophthalmologic apparatus acquiring data of a fundus of a subject's eye optically, comprising:
   a fixation system including at least one optical element and configured to project fixation light onto an eye of a subject;
   an image acquisition unit including at least one optical element and configured to acquire an image of the fundus of the subject's eye in a state where the fixation light is projected by the fixation system;
   processing circuitry configured as a specifying unit configured to analyze the image acquired by the image acquisition unit to specify an image region corresponding to a predetermined site of the fundus; and
   the processing circuitry further configured as a determination unit configured to determine whether or not the image region specified by the specifying unit is included within a predetermined range in the image acquired by the image acquisition unit, wherein the predetermined range is a range set based on determination range information representing a determination range for determining whether or not the subject's eye is in a state of fixation loss;
   a notification unit including a display unit and configured to perform notification corresponding to a determination result obtained by the determination unit; and
   the processing circuitry further configured as a controller configured to cause the notification unit to notify based on the determination result obtained by the determination unit,
   wherein, when the determination unit determines that the image region is included within the predetermined range, a fixation position adjustment operation object for adjusting a fixation position by a touch operation is displayed on the display unit.

2. The ophthalmologic apparatus of claim 1, further comprising
   a data acquisition unit including at least one lens and configured to optically acquire the data; and
   a controller configured to cause the data acquisition unit to acquire the data when it is determined by the determination unit that the image region is included within the predetermined range.

3. The ophthalmologic apparatus of claim 2, further comprising
   a movement mechanism configured to change relative position between the subject's eye and the data acquisition unit, wherein
   the controller is configured:
   to perform alignment between the subject's eye and the data acquisition unit by controlling the movement mechanism;
   to cause the image acquisition unit to acquire the image after the alignment is completed; and;
   to cause the data acquisition unit to acquire the data when it is determined by the determination unit that the image region is included within the predetermined range.

4. The ophthalmologic apparatus of claim 3, further comprising:
   an operation unit including a user interface, wherein
   the controller is configured to cause the notification unit to perform notification and to control the movement mechanism based on an operation content on the operation unit, when it is determined by the determination unit that the image region is not included within the predetermined range.

5. The ophthalmologic apparatus of claim 2, wherein
   the controller is configured to change a projection position of the fixation light so as to guide a fixation position of the subject's eye to a predetermined fixation position by controlling the fixation system, when it is determined by the determination unit that the image region is not included within the predetermined range.

6. The ophthalmologic apparatus of claim 1, wherein
   the controller is configured to cause a message content corresponding to the determination result obtained by the determination unit to be displayed on the display unit.

7. The ophthalmologic apparatus of claim 1, wherein
   the controller is configured:
   to cause the image acquired by the image acquisition unit to be displayed on the display unit and to cause information representing the predetermined range or the image region to be displayed so as to be superimposed on the image; and
   to blink the information when it is determined by the determination unit that the image region is not included within the predetermined range.

8. The ophthalmologic apparatus of claim 1, wherein
   the controller is configured to cause information for guiding a fixation position of the subject's eye to a predetermined fixation position to be displayed on the display unit.

9. The ophthalmologic apparatus of claim 1, further comprising:
   a data acquisition unit including at least one lens and configured to optically acquire the data; and
   a controller configured to cause the data acquisition unit to acquire the data and to store the data in a storage unit in association with information corresponding to a determination result obtained by the determination unit.

10. The ophthalmologic apparatus of claim 1, wherein
    the predetermined range can be set according to the subject's eye.

11. The ophthalmologic apparatus of claim 1, wherein
    the predetermined site is an optic disc, a macular region, a blood vessel, a lesion, or a scar after treatment.

12. The ophthalmologic apparatus of claim 1, wherein the fixation position adjustment operation object displayed on the display unit includes arrows in four directions for adjusting the fixation position by the touch operation in each of the four directions.

13. A method of controlling an ophthalmologic apparatus acquiring data of a fundus of a subject's eye optically, comprising:
    projecting fixation light onto an eye of a subject using a fixation system;

acquiring an image of the fundus of the subject's eye in a state where the fixation light is projected by the fixation system;

analyzing the acquired image to specify an image region corresponding to a predetermined site of the fundus;

determining whether or not the specified image region is included within a predetermined range in the acquired image, wherein the predetermined range is a range set based on determination range information representing a determination range for determining whether or not the subject's eye is in a state of fixation loss;

performing notification to a display unit when it is determined that the image region is not included within the predetermined range; and when the determining determines that the image region is included within the predetermined range, adjusting a fixation position by a touch operation displayed on the display unit.

14. The method of controlling the ophthalmologic apparatus of claim 13, wherein the data is acquired when it is determined that the image region is included within the predetermined range.

* * * * *